US00PP25630P3

(12) United States Plant Patent
Maillard et al.

(10) Patent No.: US PP25,630 P3
(45) Date of Patent: Jun. 23, 2015

(54) APRICOT TREE NAMED 'APRINEW'

(50) Latin Name: ***Prunus armeniaca* L.**
Varietal Denomination: APRINEW

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 165 days.

(21) Appl. No.: 13/815,928

(22) Filed: Mar. 18, 2013

(65) Prior Publication Data

US 2013/0263336 P1 Oct. 3, 2013

(51) Int. Cl.
*A01H 5/08* (2006.01)

(52) U.S. Cl.
CPC ..... *A01H 5/0843* (2013.01)
USPC ..... Plt./186

(58) Field of Classification Search
USPC ..... Plt./186
See application file for complete search history.

*Primary Examiner* — Susan McCormick Ewoldt
(74) *Attorney, Agent, or Firm* — Westerman, Hattori, Daniels & Adrian, LLP

(57) ABSTRACT

A new and distinct variety of apricot tree, denominated 'APRINEW', characterized by fruits of very long shelf life without alteration after harvesting, and with an orange flesh of high eating quality, aromatic and with a high level of sugar, and with an attractive luminous red to orange red skin on an orange background.

3 Drawing Sheets

Botanical classification: *Prunus armeniaca* L.
Variety denomination: 'APRINEW'.
This application claims priority of Community plant variety right No. 2012/0748 filed on Apr. 2, 2012 (Apr. 2, 2012), which is hereby incorporated by reference in its entirety.

BACKGROUND OF THE NEW VARIETY

The present invention relates to a new and distinct variety of apricot tree, *Prunus armeniaca* L., which has been given the variety denomination 'APRINEW'. This new tree produces fruit with a long shelf life without alteration after harvesting, very good eating quality, and orange flesh fruit for fresh market in July in the Pyrénées-Orientales department (an administrative district), France. 'APRINEW' is a promising candidate for commercial success in that it has very attractive fruits with long shelf life without alteration after harvesting. This new variety results from our plant-breeding program aimed at obtaining apricot trees producing fruits of sweet and very aromatic taste, with an attractive orange fruit skin covered by an appealing red to red orange blush. One of our main concerns is also the production of new varieties producing fruits having a long shelf life after harvesting, in order to facilitate long distance shipping. Our final purpose is the production of a range of new apricot tree varieties differing by their time of maturity, while producing fruits of very similar characteristics, in order to provide markets with almost indistinguishable fruits during the whole period of production of apricot.

ORIGIN OF THE VARIETY

The 'APRINEW' apricot tree originated in a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'APRINEW' variety resulted from a pollinated cross between the 'ASFCOT0406' (U.S. Plant Pat. No. 21,136) apricot tree, which was used as a seed parent, and the 'ASFCOT0405' (U.S. Plant Pat. No. 21,137) apricot tree which was used as the pollen parent.

'APRINEW' was provisionally designated, tested and genetically identified by a genetic profile, under number 02.11.19AB and was registered at the Official Catalogue of the Agriculture Ministry of the French Republic on Nov. 27, 2011 under number 4049395. The 'APRINEW' variety was propagated by grafting on a 'FRANC INRA MONTCLAR' (non patented) rootstock. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of apricot tree blooms generally during the first fortnight of March in the Pyrénées-Orientales department, France. More particularly, it approximately blooms between March 10$^{th}$ and March 26$^{th}$, generally 6 days later than 'ASFCOT0409' (U.S. Plant Pat. No. 21,135). However, it was observed that its early date of blooming seems to be highly dependant on climatic conditions.

The first fruit of 'APRINEW' apricot tree ripens at the end of June or during the first fortnight of July, generally about 5 days later than 'ASFCOT0409' (U.S. Plant Pat. No. 21,135). However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
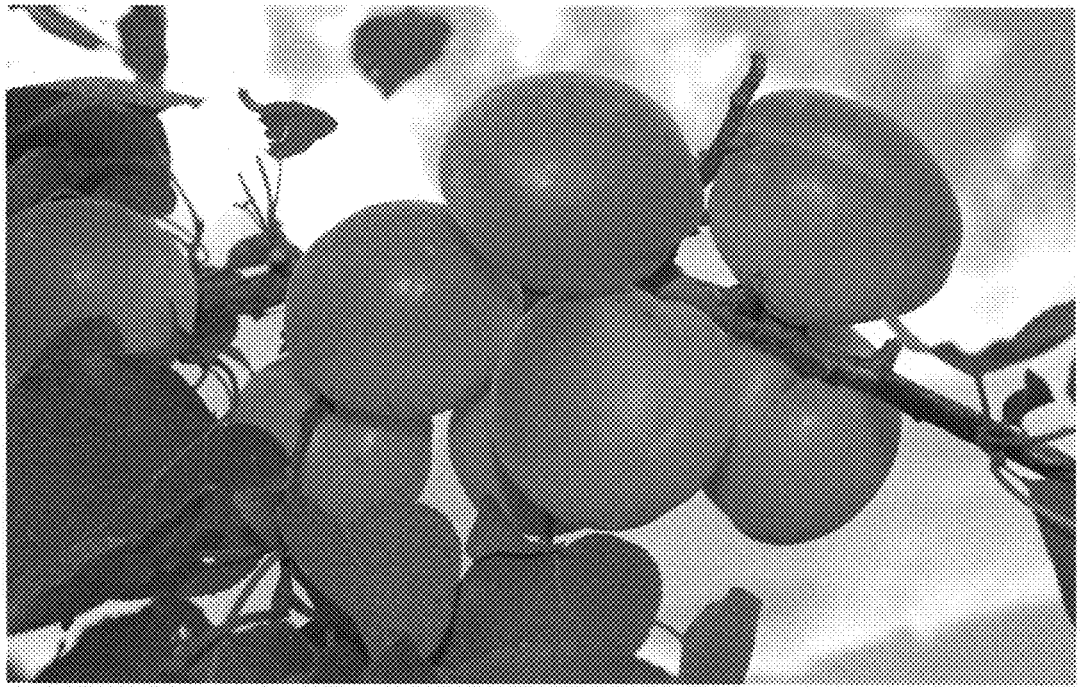
FIG. 1 is a color photograph, which shows a view of a tree of the new variety in orchard, bearing fruits.
Figure 2:
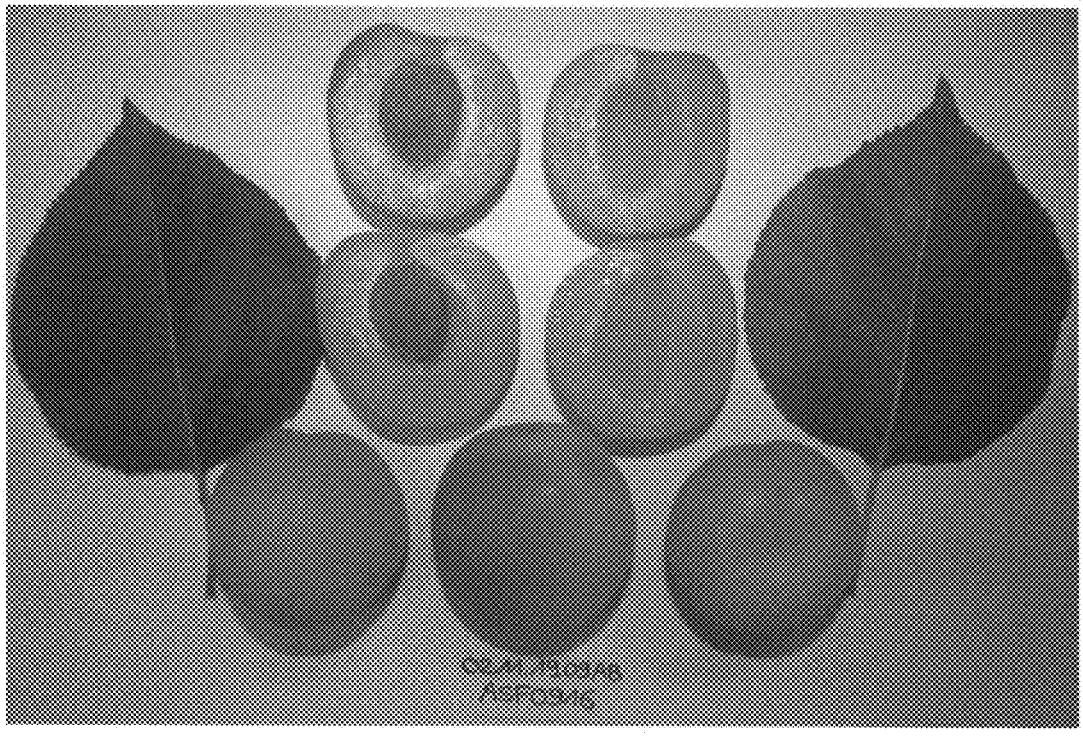
FIG. 2 is a color photograph, which shows three whole fruits and leaves of the new variety, and a fourth and a fifth fruit, cut in half, with the stone left in one of the halves for depicting the fruit flesh and the stone of the new variety.
Figure 3:
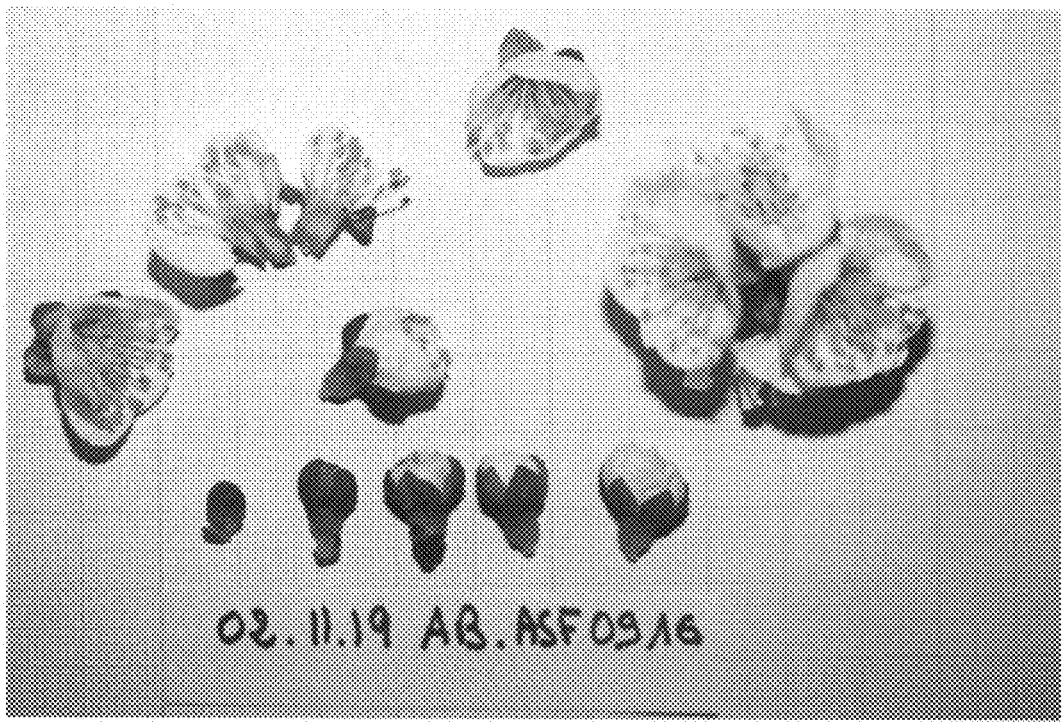
FIG. 3 is a color photograph with reverse and side views of flowers of the new variety, and, with petals removed, reproductive organs of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'APRINEW' is high, due to fruit very long shelf life without alteration after harvesting.

Trees are vigorous and large stature in a naturally semi-upright out aspect. The time of beginning of flowering is considered medium; flowering begins during the first fortnight of March. The flower petals are small and colored in white or in very pale pink. Leaf glands are present and round. Time of maturity for consumption is considered medium to late, namely at the end of June or in July. The fruit flesh is considered orange. The fruit skin is medium thick and colored with a red to red orange blush on an orange background. The stone is medium size. Fruit taste is very aromatic and with a good balance between the level of sugar and acidity.

Compared to 'ASFCOT0409' (U.S. Plant Pat. No. 21,135) apricot tree, 'APRINEW' variety blooms broadly 6 days later and ripens approximately 5 days later than 'ASFCOT0409', as set forth above. 'APRINEW' variety produces very attractive fruits, with a homogenous presentation and a luminous red orange coloration, covering more or less 35% of the fruit skin, on an orange background. 'APRINEW' fruits show a good behaviour both on the tree after growth completion and after harvesting. The time of maturity of the new variety is also interesting, because it ripens just a few days after 'ASFCOT0409' variety.

The new variety male parent which is 'ASFCOT0405' (U.S. Plant Pat. No. 21,137) blooms generally mid-March and ripens at the end of June, approximately at the same time as 'GOLDRICH' apricot variety (non patented).

The new variety female parent which is 'ASFCOT0406' (U.S. Plant Pat. No. 21,136) blooms generally at the end of March and ripens at the end of June, approximately at the same time as 'GOLDRICH' apricot variety (non patented), such as 'ASFCOT0405' variety.

DETAILED DESCRIPTION

Referring more specifically to the pomological details of this new and distinct variety of apricot tree, the following was observed on trees in their fourth year of production. under the ecological conditions prevailing at the orchards located near the town of Elne, Pyrénées-Orientales department, France. All observations have been done on rootstock cultivars. Used rootstocks were 'FRANC INRA MONTCLAR' (non patented) trees. All major color code designations are by reference to The R.H.S. Colour Chart 2001 (Fourth Edition) provided by The Royal Horticultural Society of Great Britain.

Tree:

*Size*.—Generally. — Considered large as compared to other common commercial apricot cultivars. Trees reach about 250 cm during the first growing season. Trees were pruned during each following season to a height of approximately 250 cm and to a diameter of 200 cm.

*Spread*.—Approximately 200 cm. The whole orchard was oriented to a central leader organization, with tree lines spaced of 4.0 meters and trees spaced of 1.0 meter in a same tree line.

*Vigor*.—Considered vigorous. Current season shoots growth could reach 100 cm. During the first year of growth, trees growth reaches 250 cm. In the second and following seasons, the size of trees is reduced to 250 cm by pruning. However, these characteristics are dependant on soils fertility, cultural practices, and prevailing climatic conditions.

*Productivity*.—Very Productive and regular. Fruit set is spaced by thinning to develop the remaining fruit into the desired market sized fruit. Thinning is to remove some of the fruit to unload the tree so as to maximize fruit production. Because of the fruit size, the new variety only requires a medium thinning for the tree valorisation, to obtain the maximum commercial fruit size and optimize exploitation of this variety 'APRINEW'. Thinning was necessary every year during the years of observation. The number of the fruit set varies with the prevailing climatic conditions and cultural practices employed during the bloom period, and is therefore not distinctive of the present variety.

*Bearer*.—Very regular. No alternate bearing was observed.

*Form*.—The 'APRINEW' variety has a naturally semi-upright shape.

*Density*.—Considered highly dense, in order to obtain and observe fruits more quickly.

*Fertility*.—The fertility of 'APRINEW' variety hasn't been confirm yet.

*Hardiness*.—The present tree was grown and evaluated in France. The variety appears to be hardy under the central Pyrénées-Orientales department typical climatic conditions. Experimentations on different sites with winter chilling requirement comprised between 350 hours and 1200 hours showed a good behaviour of the tree in all cases. The tree also seems to have a good resistance to frosty springtime weather.

Trunk:

*Diameter*.—Approximately between 12.0 cm and 13.0 cm in diameter when measured at a distance of approximately 30 cm above the soil level.

*Bark texture*.—Considered smooth to rough when numerous lenticels are present.

*Bark coloration*.—The bark has mostly a brown (RHS Brown 200 A to B) coloration.

*Lenticels*.—Lenticel color. — A light grey color (RHS Greyed White Group 156 A). Density. — Numerous lenticels are present, approximately 4 lenticels per $cm^2$. Size. — Lenticels are approximately 1.0 millimeters in width and 3.0 to 5.0 millimeters long.

Branches:

*Size*.—Current season shoots are considered medium for the variety. Mature branches are considered medium to large for the variety.

*Diameter*.—Average as compared to other apricot varieties. The current season shoots have a diameter from 5.0 to 7.0 millimeters, and mature branches have a diameter from 18.0 to 22.0 millimeters.

*Surface texture*.—Current season shoots have a smooth texture. Mature branches are medium rough. Roughness increases with tree age.

*Crotch angles*.—The crotch angles are generally between 45 degrees and 60 degrees from the trunk axis. At maturity, the crotch angle increases with fruits weight. This particular characteristic is not considered distinctive of the variety, however.

*Internode length*.—Generally between 14.0 millimeters and 21.0 millimeters.

*Color of mature branches*.—Brown (RHS Brown N 200 A to N 200 B).

*Color of current season's shoots*.—Considered an orange brown (RHS Greyed Orange Group 165 A) on the upper part which is exposed to sunlight, whereas the lower part of new shoot tips is colored grey brown (RHS Grey Brown 199 A). The current season's shoots color evolves and turns to mature branches color when aging.

*Vigor*.—Considered vigorous.

*Lenticels*.—Density. — Numerous lenticels are present, just as on the trunk, especially on mature branches. Size. — Considered slightly smaller than trunk's lenticels, they are approximately 0.7 millimeters wide and 3.0 millimeters long. Color. — A light grey (RHS Greyed White 156 A).

Leaves:

*Size*.—Considered medium for the species.

*Leaf length*.—Approximately 72.0 to 96.0 millimeters (average 82.0 millimeters).

*Leaf width*.—Approximately 59.0 to 64.0 millimeters (average 66.0 millimeters). Leaf form in cross section. — Concave.

*Leaf form*.—Almost circular.

*Leaf tip form*.—Acuminate.

*Leaf base form*.—Generally round to truncated.

*Leaf margins*.—Considered dentate.

*Thickness*.—Medium to thick.

*Upper surface texture*.—Smooth.

*Lower surface texture*.—Smooth.

*Leaf colour*.—Upper leaf surface. — Green (RHS Green Group 137 A to B or RHS Yellow Green 147 A). Lower surface. — A lighter green (RHS Yellow Green 146 B or RHS Yellow Green 147 B) than the upper leaf surface color.

*Leaf venation*.—Pinnately veined.

*Mid-vein*.—

*Thickness*.—Approximately 1.5 to 2.0 millimeters when measured at the base of the leaf.

*Color*.—Green (RHS Green 143 B).

*Other veins color*.—Similar as mid-vein color.

*Uniformity*.—Leaves are of medium size and generally found alone. No stipules are generally found.

*Leaf petioles*.—Size. — Generally large. Length. — Between 48.0 and 62.0 millimeters. Diameter. — Approximately 1.5 to 2.0 millimeters. Surface. — Generally smooth and slightly ribbed on upper face.

*Petioles colour*.—Upper petiole surface. — Depending on climatic conditions and sunlight exposure, the anthocyanic coloration on petiole's upper surface can be very deep and varies from red (RHS Greyed Red 178 A) to purple red (RHS Greyed Purple 183 A to B).

*Leaf glands*.—Size. — Considered medium. Length. — Approximately 0.7 to 0.9 millimeters. Width. — Approximately 0.7 to 0.9 millimeters. Number. — Between 2 and 4 glands per leaf. Generally 3 glands per leaf. Type. — Round. Position. — Alternate between upper portion of petiole and lower portion of leaf blade. Color. — Generally grey orange (RHS Greyed Orange Group 165 A).

*Leaf stipules*.—Generally. — No leaf stipules were observed.

Flowers:

*Flower buds*.—Generally. — At pre-floral stage of development, the floral buds are conic in form with a very rounded tip (ball shaped). Their form is evolving until blooming, with variables dimensions. Just before blooming, floral buds are approximately 10.0 millimeters wide and approximately 15.0 millimeters long. Generally, a bud is found alone or in group of two buds. Color. — This characteristic is dependent upon the proximity to bloom. At pre-floral stage of development, the bottom of the flowers buds, formed by the sepals, is of purple-brown color (RHS Greyed Purple 183 B to C); the corolla, formed by the petals, is generally of white color with a very slightly pink pigmentation (RHS White Group N 155 B to C).

*Texture*.—Smooth and glabrous.

*Hardiness*.—The buds are considered hardy under typical central Pyrénées-Orientales department climatic conditions. No winter injury was noted during the last several years of evaluation in the central Pyrénées-Orientales department, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Pedicel*.—Length. — About 3.0 to 5.0 millimeters. Width. — About 2.0 millimeters.

*Flower shoots of leaf buds*.—Form. — Ovoid. Length. — About 2.0 millimeters. Width. — About 1.5 millimeters. Color. — Orange grey (RHS Greyed Orange 175 A).

*Flower shoots of flower buds*.—Form. — Ovoid. Length. — About 2.0 millimeters. Width. — About 1.5 millimeters. Color. — Orange grey (RHS Greyed Orange 175 A).

*Date of bloom*.—Generally in March.

*First bloom*.—The first bloom was observed on Mar. 15, 2006.

*Petal fall*.—Mar. 25, 2006.

*Blooming time*.—Considered medium season in relative comparison to other commercial apricot cultivars grown in the Pyrénées-Orientales department, France. Thus, the first blooming time was from Mar. 15 to Mar. 25, 2006. Some of the next observed blooming periods were from Mar. 25 until Mar. 30, 2010, then from Mar. 10 to Mar. 16, 2011 and from Mar. 26 until Apr. 3, 2012.

*Flower type*.—The variety is considered to have a showy type of flower.

*Duration of bloom*.—Approximately 6 to 10 days.

*Flower size*.—Flower diameter at full bloom is approximately 20.0 to 25.0 millimeters.

*Bloom quantity*.—Considered abundant, flowers are generally found in bunches.

*Flower bud frequency*.—Generally 1 flower bud or several flower buds per groups of 2 to 3.

*Petal size*.—Generally. — Small. Length. — Generally about 13.0 millimeters. Width. — Generally about 14.0 millimeters.

*Petal form*.—Round-shaped.

*Petal count*.—Generally 5 or 6, overlapping with sepals.

*Petal texture*.—Smooth and soft.

*Petal color*.—Both surfaces of petals are colored with a white (RHS White N 155 B to C) to a very light pink (RHS Greyed Purple 186 D) color.

*Fragrance*.—Moderate.

*Petal margins*.—Slightly wavy especially near the base.

*Petal base*.—Narrow at point of attachment.

*Petal apex*.—Wide-dome shaped.

*Petal peduncle*.—Length. — Approximately 3.0 to 5.0 millimeters. Diameter. — Approximately 2.0 millimeters. Color. — Generally yellow green (RHS Yellow Green 145 B to C).

*Sepals*.—Size. — Generally considered small. Length. — Approximately between 5.0 and 6.0 millimeters. Width. — Approximately between 4.0 and 6.0 millimeters. Sepal count. — Generally 5, sometimes 6. Form. — Triangular, with a slightly pointed apex. Color. — Generally, both surfaces of sepals are colored with a purple brown (RHS Greyed Purple 184 B to C or RHS Greyed Purple 185 B to C) color.

*Stamens*.—Average number of stamen per flower. — Approximately 30 stamens per flower. Length. — Medium.

*Filaments*.—Size. — Approximately between 7.0 and 12.0 millimeters in length. Color. — White (RHS White Group N 155 B).

*Anthers*.—Color. — Orange Yellow (RHS Yellow Orange 16 A to B).

*Pistil*.—Number. — Usually 1. Length. — Approximately 15.0 to 17.0 millimeters including the ovary. Generally stigmas are at the same level as anthers or above. Color. — Considered white (RHS White 155 C) or very pale green (RHS Yellow Green 145 D). Pubescence. — Present.

*Pollen*.—Pollen production. — Pollen is abundant. The fertility has not been check yet. Color. — Orange yellow color (RHS Yellow Orange 16 A to B).

*Filaments size*.—Approximately between 7.0 and 12.0 millimeters.

*Calyx*.—Internal surface texture. — Smooth. Color. — The inner surface of the calyx is considered orange (RHS Yellow Orange 24 A or RHS Yellow Orange 25 A) whereas the outer surface is purple (RHS Greyed Purple 185 B to C) becoming slightly lighter near calyx base.

Fruit:

*Maturity*.—Considered medium to late season. Generally, fruits become mature during the first fortnight of July.

*Date of first picking*.—Jul. 1, 2006.

*Date of last picking*.—The date of harvest varies slightly with the prevailing climatic conditions. The 'APRINEW' variety has late date of picking and a grouped maturity. The maturity is grouped within 4 to 9 days and the harvest is generally performed in two runs. The first picking was carry on from Jul. 1 to Jul. 9, 2006. Last other known picking times were from Jul. 2 to Jul. 6, 2009, Jul. 14 to Jul. 23, 2010, then from Jun. 25 until Jun. 29, 2011 and from Jul. 10 to Jul. 16, 2012.

*Size*.—Generally. — Considered medium to large. Length. — Approximately 53.0 to 58.0 millimeters. Width. — Approximately 50.0 to 53.0 millimeters. Thickness. — Approximately 47.0 to 52.0 millimeters.

*Typical weight*.—Generally between 71.0 and 86.0 grams. This characteristic is high dependent upon the prevailing cultural practices, and therefore is not particularly distinctive of the variety.

*Fruit form*.—Generally. — Round and slightly oblong near the apex and at the fruit base. The fruit is considered to be symmetrical.

*Suture*.—Generally. — Slightly marked, extending from the base to the apex. The suture is more distinct, almost slightly wide mouthed around the stem. Color. — The suture has generally a color similar to the whole fruit color. The suture is colored with a red to red orange (RHS Orange Red N 34 A to RHS Orange Red 34 A).

*Ventral surface*.—Form. — Round.

*Apex*.—Flat to slightly retuse.

*Base*.—Straight to slightly wide-mouthed.

*Stem cavity*.—Shallow. Average depth of the stem cavity is about 7.0 to 9.0 millimeters. Average width is about 10.0 to 12.0 millimeters.

*Stem*.—Size. — Generally small. Stem length is about 5.0 to 6.0 millimeters. Stem diameter is about 2.5 millimeters. Color. — Stem color is generally green (RHS Yellow Green 145 B).

*Fruit skin*.—Thickness. — Considered medium. Texture. — Smooth. Pubescence. — Present but very light, almost non-existent. Tendency to crack. — None observed.

*Color*.—Blush color. — This blush color is a red to orange red (RHS Orange Red N 34 A to RHS Orange Red 34 A). The orange red blush covers more or less 35% of the fruit skin surface for fruits that are exposed to sunlight. The percentage of the blush on the fruit skin surface can vary, and is generally dependant upon the prevailing conditions under which the fruit was grown. Ground color. — The ground color covers more or less 65% of the fruit skin surface, and is considered orange yellow (RHS Orange 26 A or RHS Orange 25 B). Adherence to flesh. — Very adherent. Taste. — Very slightly acid, with a high level of sugars.

*Flesh*.—Ripens. — Homogenously. Texture. — Fine and firm. Very melting and juicy at end of maturity. Fibers. — Generally none observed. Aroma. — Very present, pronounced. Firmness. — Firm and melting. Holds firmness over the time. Eating quality. — Considered very good and with a high level of sugars. Flavor. — Considered very good. Good balance between sugar and acidity. Very aromatic. Juice. — Very juicy. The juiciness increases with maturity. Brix. — Generally superior to 17.0 degrees, between 17.0 and 20.0 degrees. This characteristic varies slightly with the number of fruit per tree, prevailing cultural practices and the surrounding climatic conditions. Flesh color. — Considered orange (RHS Orange 25 B or RHS Orange 26 A to B).

Stone:

*Stone cavity*.—Color. — Orange (RHS Orange Group 26 A to B). Length. — Approximately 37.0 millimeters. Diameter (in parallel to the suture). — Approximately 25.0 millimeters.

*Stone type*.—Free, but the stone seems to be slightly attached to the flesh through its base.

*Size*.—Considered medium for the variety. The stone size varies depending upon the tree vigor, crop load and prevailing growing conditions. Length. — Approximately 26.0 to 29.0 millimeters. Width. — Approximately 20.0 to 22.0 millimeters. Diameter. — Approximately 11.0 to 13.0 millimeters.

*Stone form* (*viewed from stem end*).—Ovate flattened.

*Stone base shape*.—Round to slightly concave.

*Stone apex shape*.—Round, generally no point is observed.

*Stone surface*.—Surface texture. — Somewhat bumpy to smooth. Ridges at stone surface. — The ridges are present on both sides of the stone. A ridge is generally narrow. The ridges begin at the base and are extending all along the stone length.

*Stone color*.—The color of the dry stone is generally considered a greyed orange (RHS Greyed Orange 164 B).

*Tendency to split*.—Splitting is absent.

*Kernel*.—Taste. — Bitter. Size. — Medium. Length. — Approximately 18.0 millimeters. Width. — Approximately 12.0 millimeters. Thickness. — Approximately 7.0 millimeters. Form. — Ovate. Color. — The kernel skin is a greyed orange (RHS Greyed Orange 165 B). The almond, which is the seed of the kernel, is considered white (RHS White 155 B).

Type of reproduction: The variety 'APRINEW' is self-fertile, so there is no requirement for pollination.

Use: The subject variety 'APRINEW' is considered to be a apricot tree with a medium to late season maturity, and which produces fruits that are considered firm, attractively and luminously colored. Fruits have a balanced taste between acidity and sugar. They are excellent for uncooked or cooked consumption, melting and juicy when at full maturity. Fruits have excellent gustative qualities and are very aromatic. They are also useful for both local markets and very long distance shipping.

Keeping quality: Good. Fruits are well preserved during at least 3 weeks after harvest in a cold atmosphere. Fruits are considered to have a long shelf life after harvesting without alteration.

Shipping quality: Considered good. The fruit of the new apricot variety showed very little skin scarring or flesh bruises in picking, packing and shipping trials.

Resistance to insects and disease: No particular susceptibilities were noted. Under meticulous observations during planting, growing and harvesting of fruits, no particular resistance or sensitivity to plant or fruits diseases were noticed. Any variety, observed during indexing of plant characteristics, with abnormal fungus, bacterial virus or insect sensitivity is destroyed and eliminated from our breeding program.

Although the new variety of apricot tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of apricot tree as illustrated and described, characterized by fruits of very long shelf life without alteration after harvesting, and with an orange flesh of high eating quality, aromatic and with a high level of sugar, and with an attractive luminous red to orange red skin on an orange background.

* * * * *